(12) United States Patent
Fagan (10) Patent No.: US 11,806,060 B2
(45) Date of Patent: Nov. 7, 2023

(54) BONE SCREW WITH INTERNAL EXTENDABLE TANG

(71) Applicant: Orthopedic Designs North America, Inc., Tampa, FL (US)

(72) Inventor: Lance Fagan, Tampa, FL (US)

(*) Notice: Subject to any disclaimer, the term of this patent is extended or adjusted under 35 U.S.C. 154(b) by 266 days.

(21) Appl. No.: 17/174,614

(22) Filed: Feb. 12, 2021

(65) Prior Publication Data

US 2022/0257295 A1 Aug. 18, 2022

(51) Int. Cl.
*A61B 17/86* (2006.01)

(52) U.S. Cl.
CPC ............ *A61B 17/86* (2013.01); *A61B 17/864* (2013.01); *A61B 17/8635* (2013.01); *A61B 2017/8655* (2013.01)

(58) Field of Classification Search
CPC .............. A61B 17/7266; A61B 17/844; A61B 2017/8655
See application file for complete search history.

(56) References Cited

U.S. PATENT DOCUMENTS

| 2006/0064098 | A1* | 3/2006 | Hansson | A61B 17/7266 |
| | | | | 606/62 |
| 2012/0197315 | A1* | 8/2012 | Kim | A61B 17/8685 |
| | | | | 606/305 |
| 2015/0250506 | A1* | 9/2015 | Philippon | A61B 17/864 |
| | | | | 606/64 |

* cited by examiner

*Primary Examiner* — Olivia C Chang
(74) *Attorney, Agent, or Firm* — Larson & Larson; Justin P. Miller; Frank Liebenow (57) ABSTRACT

The bone screw with internal extendable is a bone screw with an internal, extendable tang. The tang—part of a tang system—is concealed within the body of the screw until after placement. After the screw is threaded into the bone, the internal tang system is pushed out of the bone screw body, forcing one or more tangs to extend out of the body and into the bone. A driver allows the user to control the different steps of insertion, including converting rotational motion of a knob into linear motion of a rod, the rod moving through the screw body to force the tang to exit the bone screw body. The one or more tangs preferably exit the bone screw body at a tang exit portal formed by one or more tang exit guide surfaces.

10 Claims, 8 Drawing Sheets

BONE SCREW WITH INTERNAL EXTENDABLE TANG

FIELD

This invention relates to the field of bone fixation hardware, specifically a screw for bones.

BACKGROUND

As part of modern surgery, hardware is used to stabilize bones. For example, plates are affixed to bones to stabilize fractures.

Screws are a means of attaching such hardware to a bone.

While screws are straightforward to use, screws can loosen over time due to expansion of the hole, or the screw rotating out.

What is needed is a screw that can be fixed in place after insertion into a bone.

SUMMARY

The bone screw with internal extendable tangs is a bone screw with an internal, extendable tang. The tang—part of a tang system—is concealed within the body of the screw until after placement.

After the screw is threaded into the bone, the internal tang system is pushed out of the bone screw body, forcing one or more tangs to extend out of the body and into the bone.

A driver allows the user to control the different steps of insertion, including converting rotational motion of a knob into linear motion of a rod, the rod moving through the screw body to force the tang out of the bone screw body.

The one or more tangs preferably exit the bone screw body at a tang exit portal formed by one or more tang exit guide surfaces. The tangs are connected to a core, the core stays within the bone screw even after extension of the one or more tangs.

The shapes of the tang exit portal and tang exit guide surfaces control the direction or directions the tangs extend and amount of curvature.

To state this differently, the tangs are linear/straight when within the bone screw body, and bend as they are extended.

Thus, the portal and guide surfaces shape the tangs, changing their straight shape to a curved shape. The result is that the tang is not limited to extending along the axis of the bone screw body, but can extend at an angle with respect to the bone screw body. By extending at an angle, the extended tang or tangs help to resist rotation of the bone screw.

The tangs are optionally removable. By using a modified version of the driver, the rod used to extend the tangs is replaced with a rod that has a threaded tip. This threaded tip interfaces with the core of the tang system, allowing the tang system, and tang, to be pulled back into the screw body.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
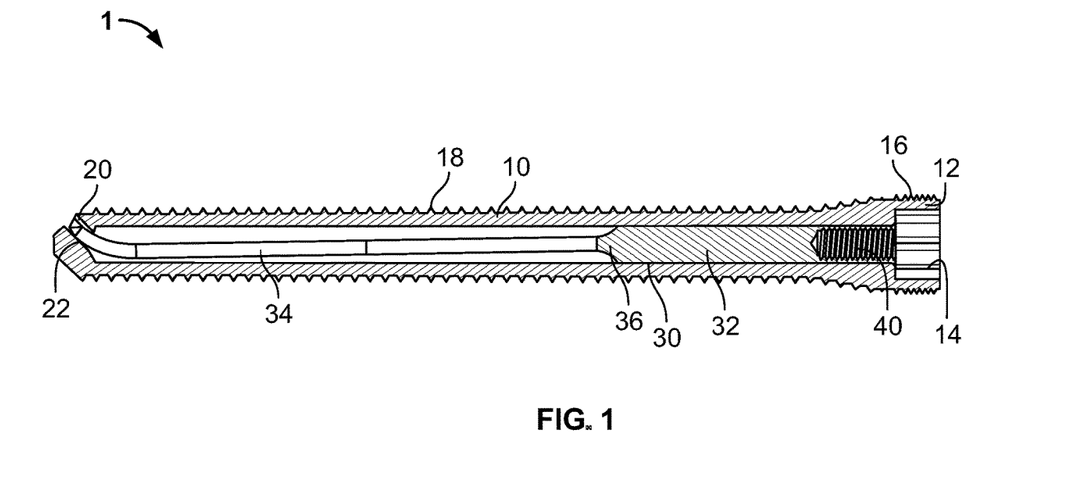
FIG. 1 illustrates a first cross-sectional view, prior to tang extension, of the bone screw with internal extendable tang.
Figure 2:
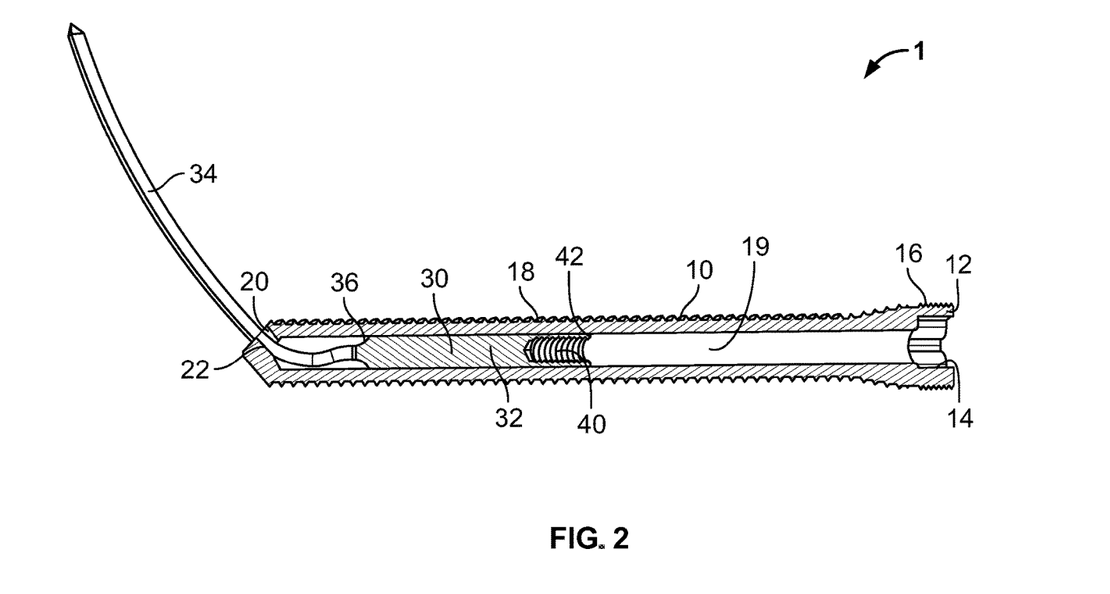
FIG. 2 illustrates a second cross-sectional view, after tang extension, of the bone screw with internal extendable tang.

Referring to FIGS. 1 and 2, a first cross-sectional view, prior to, and after, tang extension of the bone screw with internal extendable tang are shown.

The bone screw with internal extendable tang 1 is shown with bone screw body 10 formed from head 12, drive 14, gripping threads 16, external threads 18, internal channel 19, tang exit portal 20, and tang exit guide surfaces 22.

The tang system 30 is formed form core 32, tang 34, optional removal threads 40, and interface surface 42.

In the extended position in FIG. 2, the tang 34 has moved through the tang exit portal 20 and tang exit guide surfaces 22. The tang 34 was deformed during its exit, deforming from matching the axis of the bone screw body 10 to being at an angle to the bone screw body 10, thus better acting to prevent rotation of the bone screw with internal extendable tang 1.

Figure 3:
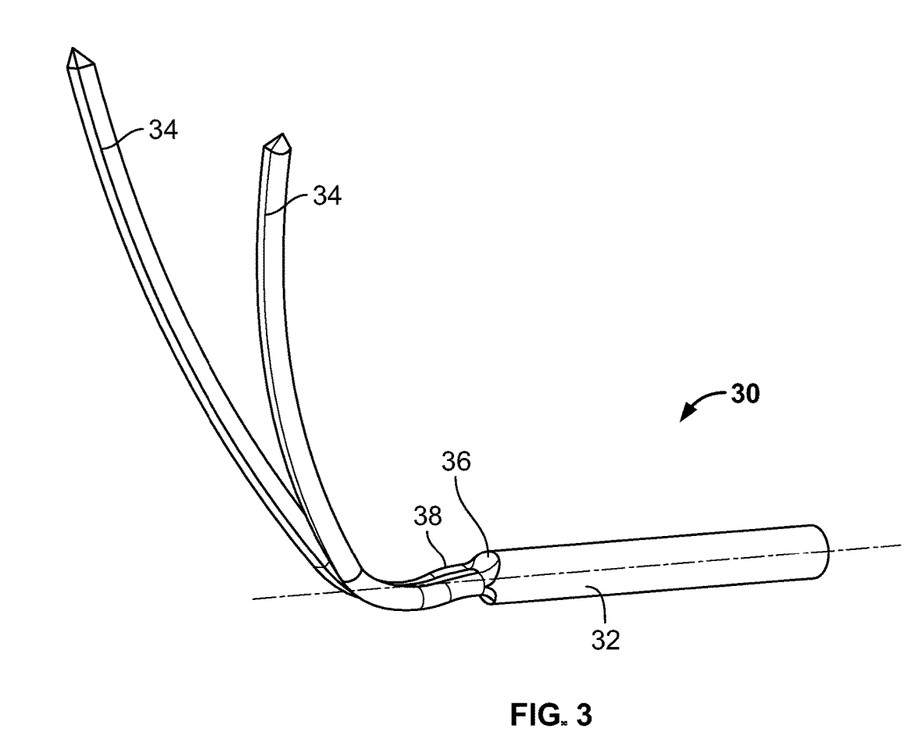
FIG. 3 illustrates an isometric view of the tang system, after extension, of the bone screw with internal extendable tang.
Figure 4:
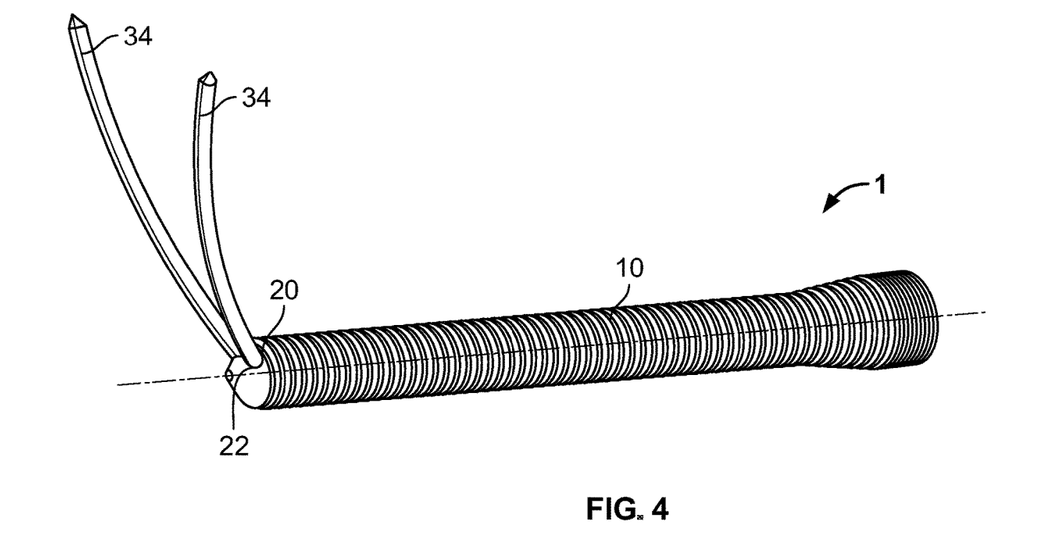
FIG. 4 illustrates an isometric view, after tang extension, of the bone screw with internal extendable tang.

Referring to FIGS. 3 and 4, an isometric view of the tang system, both with and without the bone screw body, is shown.

The tang system 30 includes a core 32 that narrows at taper 36 to optional split 38, ending in one or more tangs 34.

Before and after extension, the core 32 remains within the bone screw body 10, with the one or more tangs pushing through the tang exit portal 20, guided by the tang exit guide surfaces 22.

While the preferred embodiment includes two tangs 34 that extend in a nearly parallel arrangement, it is anticipated that the tangs 34 extend in differing directions, or that three or more tangs 34 are included.

Figure 5:
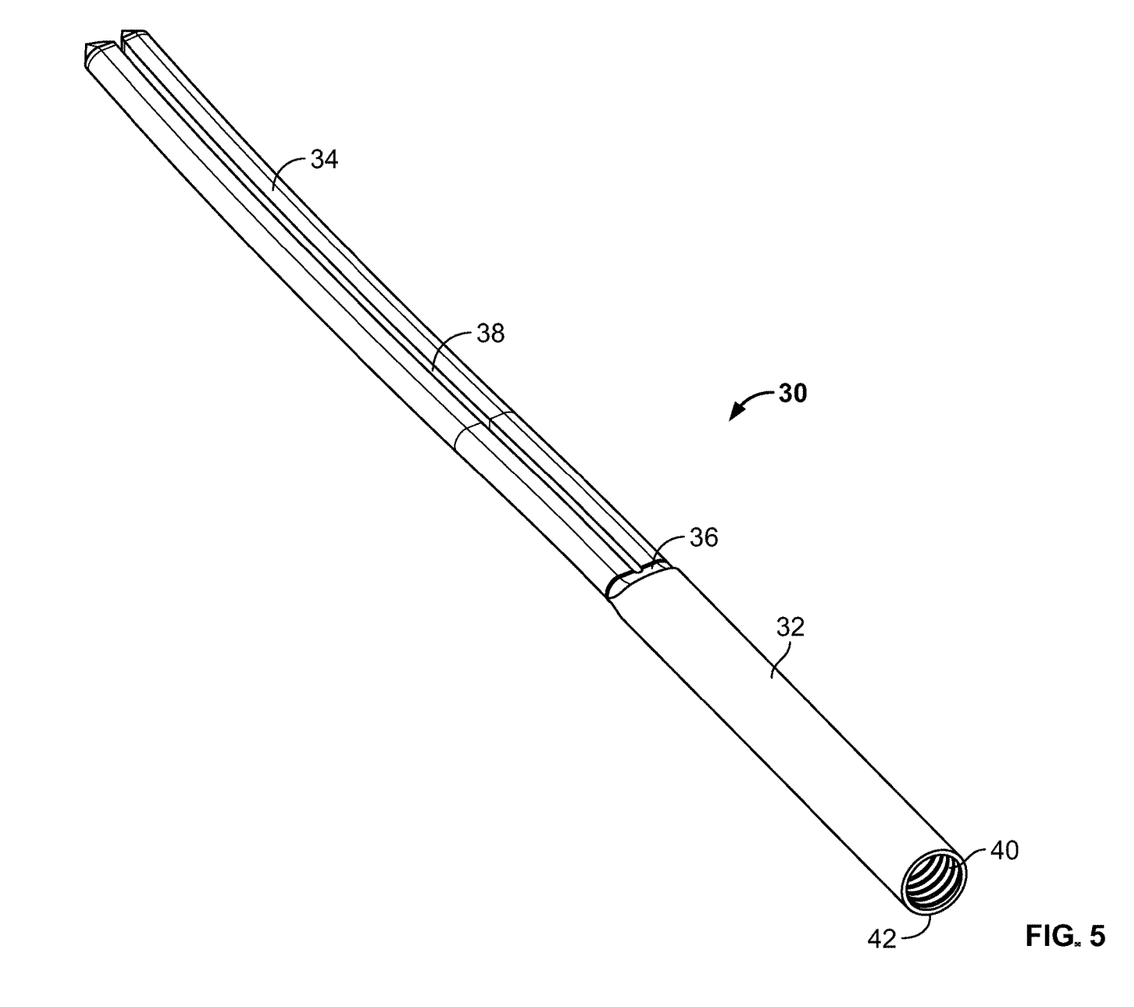
FIG. 5 illustrates an isometric view of the tang system, prior to extension, of the bone screw with internal extendable tang.

Referring to FIG. 5, an isometric view of the tang system, prior to extension, of the bone screw with internal extendable tang is shown.

The tang system 30 includes a core 32, with one or more tangs 34. If there are two or more tangs 34, there is one or more split 38.

The tang system 30 optionally includes a diameter reduction at taper 36 to result in a more deformable tang 34 and less-deformable core 32.

Also shown are removal threads 40 that allow a modified driver to grip the tang system 30 for removal.

Figure 10:
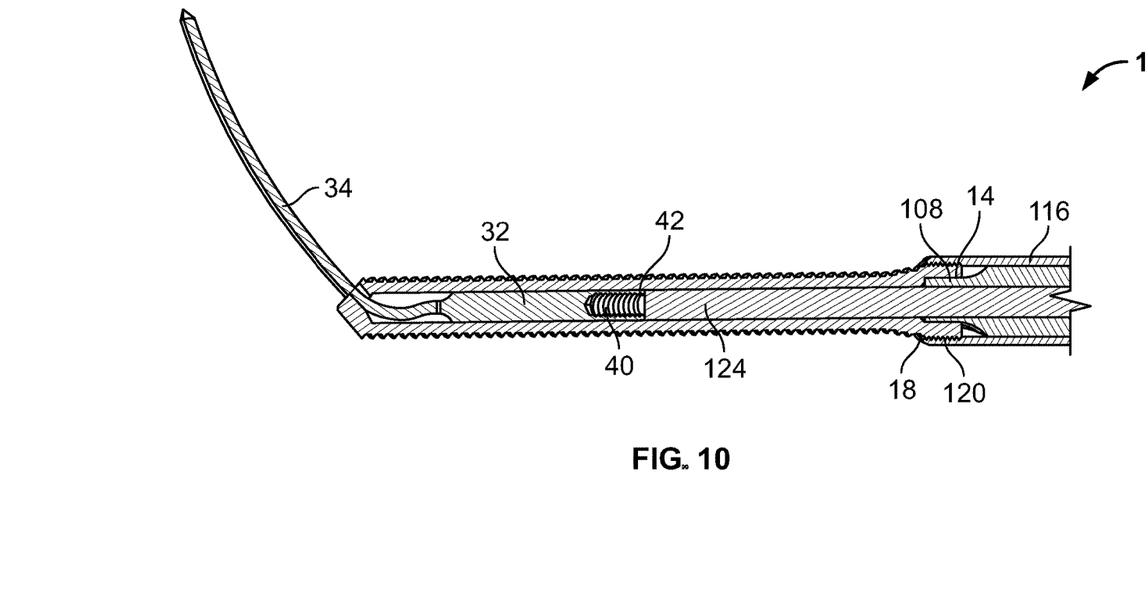
FIG. 10 illustrates a cross-sectional view, including the tip of the driver, of the bone screw with internal extendable tang.

The interface surface 42 is the surface against which the driver 100 (see FIG. 8) rests to force the tang system 30 out of the bone screw body 10 (see FIG. 10).

Figure 6:
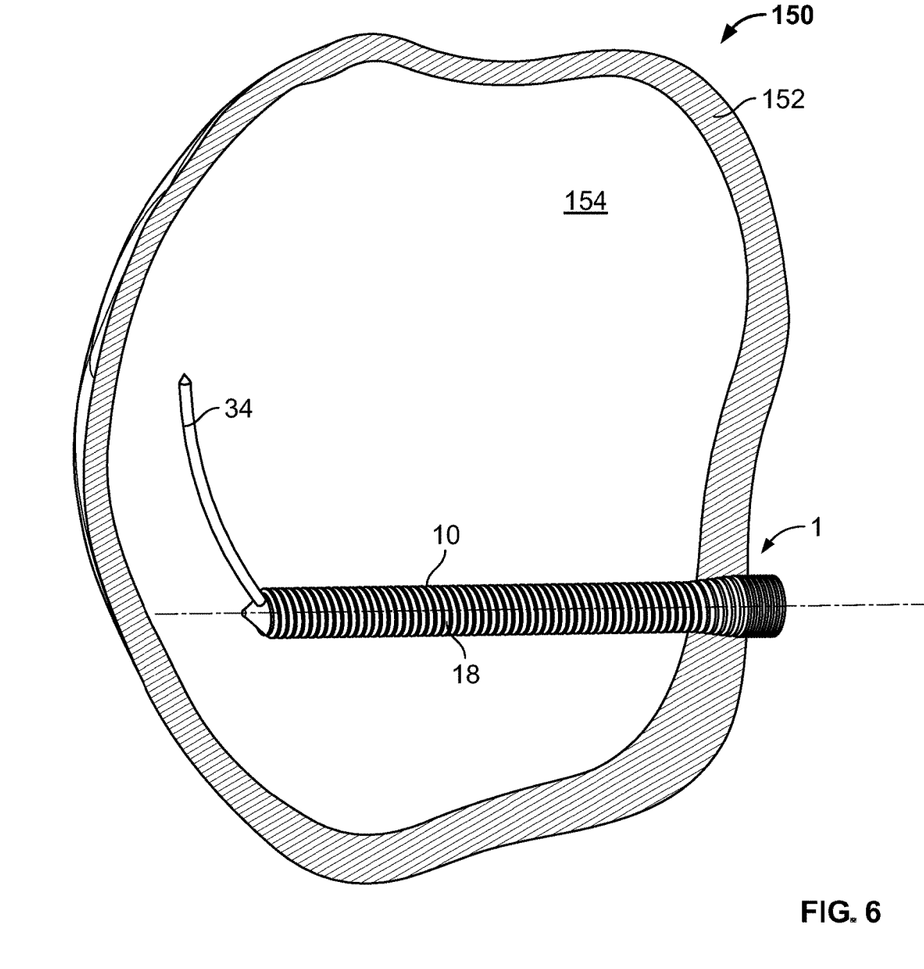
FIG. 6 illustrates a view after placement into a bone of the bone screw with internal extendable tang.

Referring to FIG. 6, a view after placement into a bone of the bone screw with internal extendable tang is shown.

The bone screw with internal extendable tang 1 is shown with bone screw body 10, the external threads 18 and tang 34 within the spongy bone 154 of the bone 150. The bone screw body 10 also shown interfaced with the compact bone 152.

Figure 7:
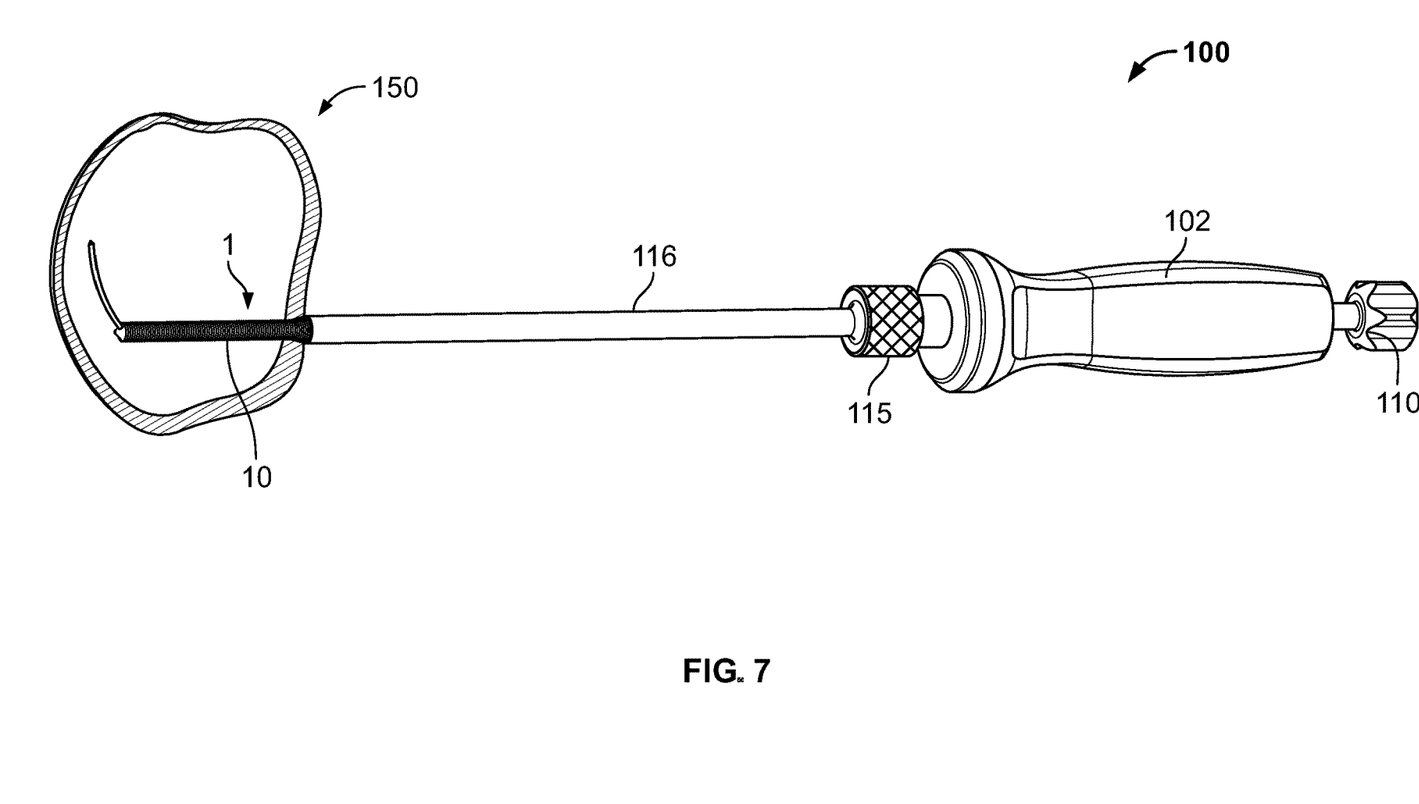
FIG. 7 illustrates a view after placement into a bone, including the driver, of the bone screw with internal extendable tang.
Figure 8:
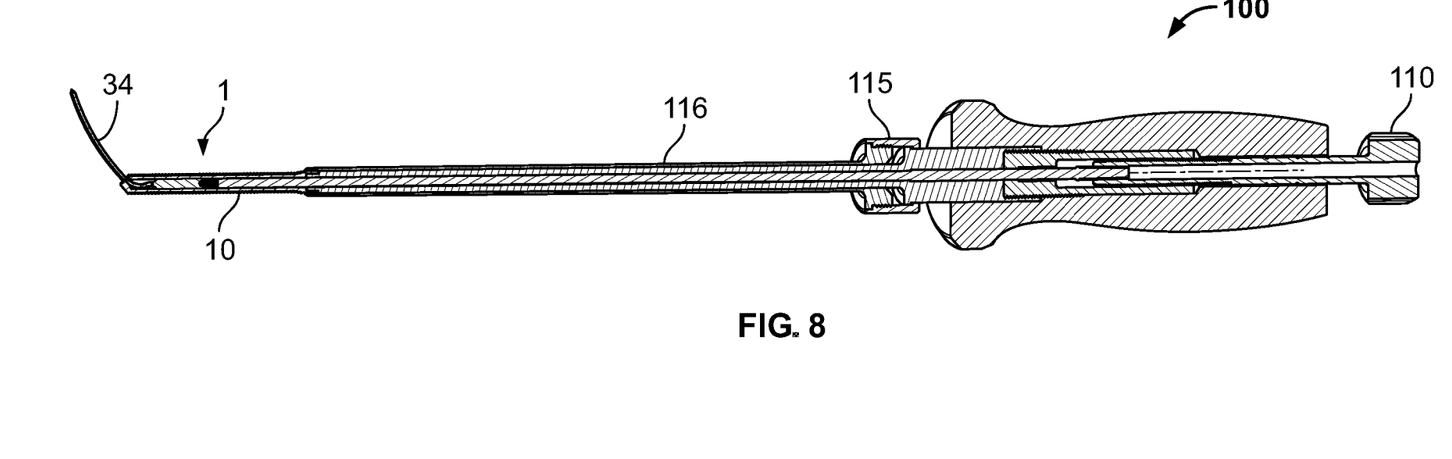
FIG. 8 illustrates a cross-sectional view, including the driver, of the bone screw with internal extendable tang.

Referring to FIGS. 7 and 8, an outer view and cross-sectional view after placement into a bone, including the driver, of the bone screw with internal extendable tang are shown.

The bone screw with internal extendable tang 1 is within bone 150. The driver 100 includes grip 102, with parts tang deployment knob 110, sleeve knob 115, and sleeve 116.

Rotation of the sleeve knob 115 threads the sleeve 116 over the bone screw body 10.

Rotation of the tang deployment knob 110 forces the tangs 32 out of the bone screw body 10.

Figure 9:
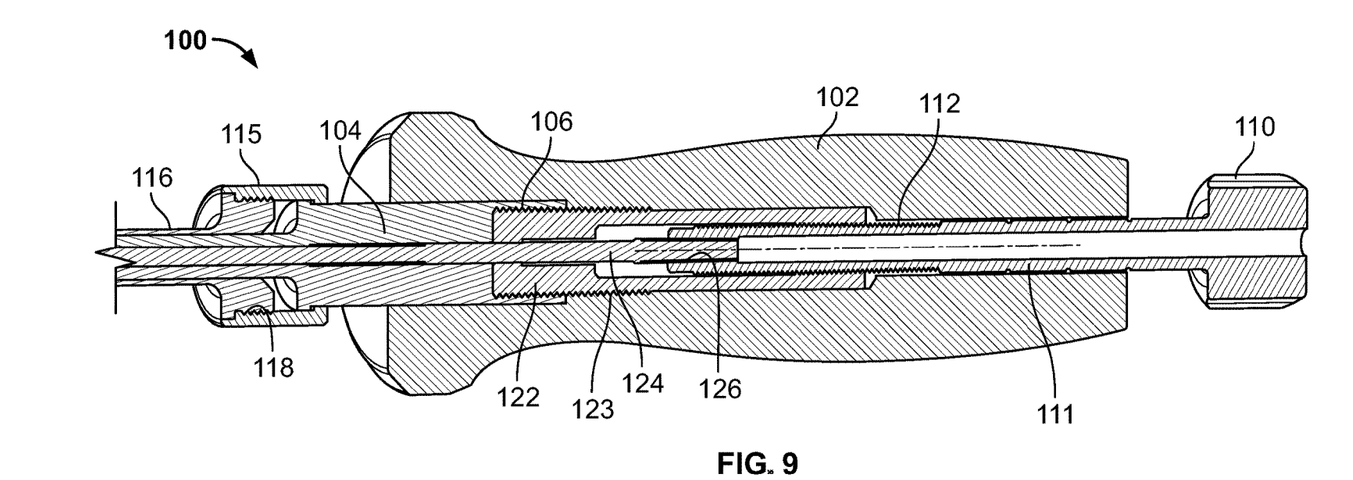
FIG. 9 illustrates a cross-sectional view of the driver of the bone screw with internal extendable tang.

Referring to FIGS. 9 and 10, a cross-sectional view of the driver, and bone screw, of the bone screw with internal extendable tang, are shown.

To interface the driver 100 with the bone screw with internal extendable tang 1, the user rotates the sleeve knob 115, which in turn rotates the sleeve 116 that is mated using threads at the sleeve proximal threads 118. The sleeve 116 rotation in turn causes the sleeve distal threads 120 to surround the external threads 18 of the bone screw body 10, locking the devices together.

To drive the bone screw with internal extendable tang 1 into the bone, the user rotates the driver 100, which includes a grip 102 that partially surrounds a fixed shank 104, which rotates shank tip 108, which rotates the drive 14 of the bone screw body 10, thus rotating the bone screw with internal extendable tang 1.

The shank 104 also includes shank head 106 that is permanently threaded into the deployment core 122. The deployment core is permanently threaded into the grip 102 at the deployment core internal threads 123.

Rotation of the tang deployment knob 110 rotates the tang deployment shaft 111, interfacing with the deployment core 122 at the knob external threads 112, and the tang extension rod 124 at the tang extension rod threads 126.

The result is an accelerated transition of rotational motion to linear motion—the tang deployment shaft 111 advances with rotation, and the tang extension rod 124 advances, with the two working together to multiply the linear motion.

The tang extension rod 124 rests against the interface surface 42, pushing through the bone screw body 10 to force the core 32 to move and push the tang 34 outward.

Figure 11:
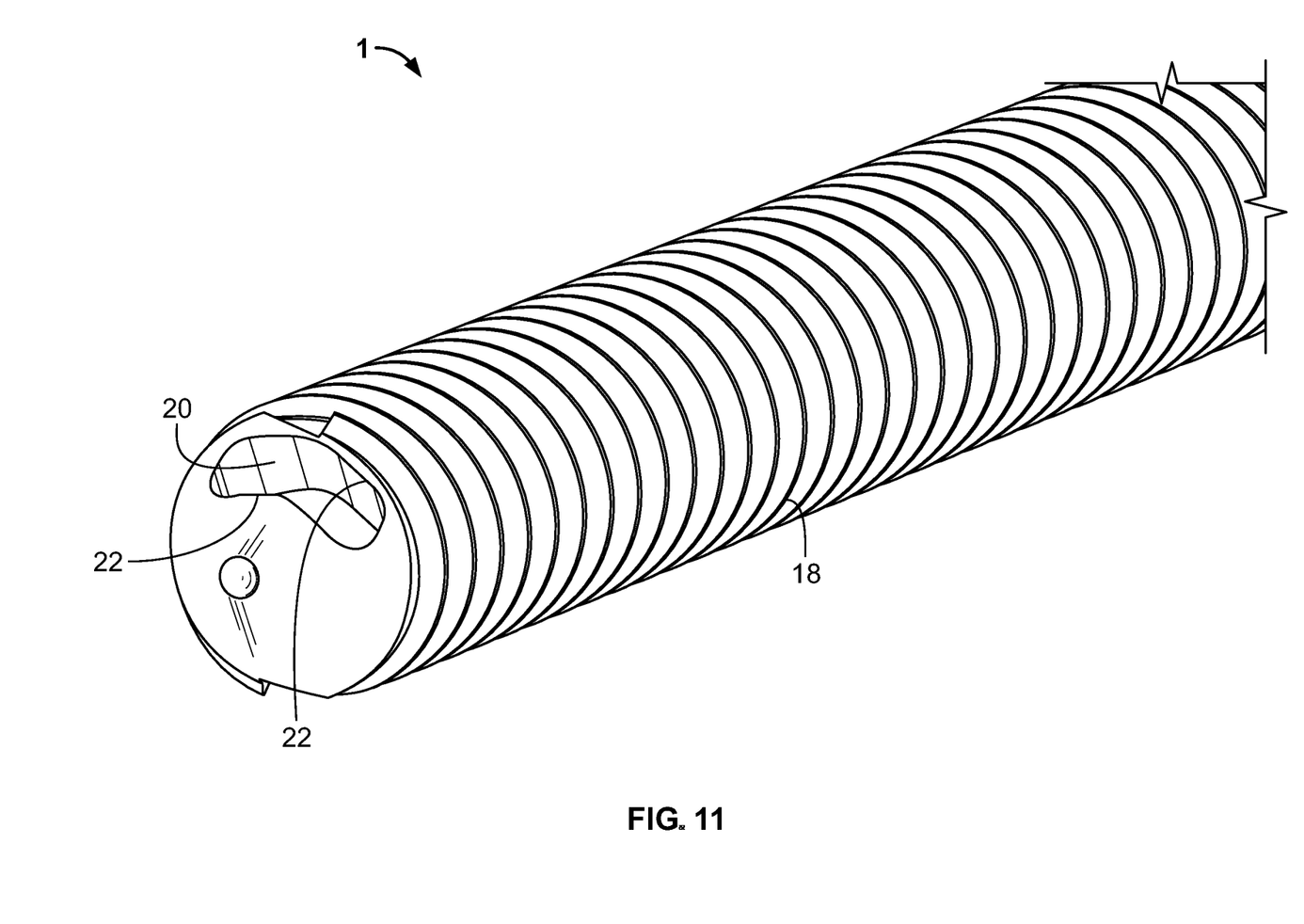
FIG. 11 illustrates a view of the tip of the bone screw with internal extendable tang.

Referring to FIG. 11, a view of the tip of the bone screw with internal extendable tang is shown.

The bone screw with internal extendable tang 1 includes external threads 18, and ends in one or more tang exit portal 20 with tang exit guide surfaces 22.

The tang exit guide surfaces 22 are shown forming an inverted U-shape, but other shapes are anticipated as needed to direct the tangs 34 as they exit the bone screw body 10.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A screw for fastening into a bone, the screw comprising:
   a body;
      an internal channel within the body;
   a tang system sliding within the internal channel;
      the tang system including a first tang and a second tang;
      the first tang having a first position within the body, and a second position extending beyond the body;
      the second tang adjacent to the first tang when the first tang is in the first position;
      the second tang separated from the first tang when the first tang is the second position;
   a single shared tang exit portal;
      the single shared tang exit portal being U-shaped;
      the first tang and the second tang passing through the single shared tang exit portal when moving between the first position within the body, and the second position extending beyond the body;
      the first tang and second tang at an acute angle with respect to each other in the second position;
   one or more tang exit guide surfaces within the single shared tang exit portal;
      the one or more tang exit guide surfaces changing a shape of the first tang as it moves to the second position, causing the first tang to bend;
   whereby after the screw is threaded into the bone, the first tang is extended beyond the body, fixing the screw in place.

2. The screw of claim 1, wherein:
   the second position of the first tang is not parallel to the body, but instead extended at an angle with respect to the body;
   whereby the first tang prevents rotation of the body.

3. The screw of claim 1, further comprising:
   the one or more tang exit guide surfaces interfacing with the first tang as it extends beyond the body and the second tang as it extends beyond the body, causing the first tang and the second tang to change from a straight shape to a curved shape.

4. The screw of claim 1, wherein the tang system further comprises a core;
   the core including removal threads;
      the removal threads interfacing with a driver;
   whereby a user can use the driver to interface with the removal threads, pulling the tang system back into the body to permit removal of the body from the bone.

5. A device with an externally-threaded body, the device comprising:
   a first internal extendable tang as part of a tang system;
      the first internal extendable tang sliding within an internal channel, the internal channel within the externally-threaded body;

the first internal extendable tang able to be fully surrounded by the externally-threaded body in a first position, and then to extend beyond the externally-threaded body to affix into a bone in a second position;
the tang system includes a second internal extendable tang;
the second internal extendable tang adjacent to the first internal extendable tang when the first internal extendable tang is in the first position;
the second internal extendable tang separated from the first internal extendable tang when the first internal extendable tang is in the second position;
a tang exit portal;
the first internal extendable tang passing through the tang exit portal when moving between the first position within the externally-threaded body, and the second position extending beyond the externally-threaded body;
one or more tang exit guide surfaces;
the one or more tang exit guide surfaces changing a shape of the first internal extendable tang as it moves to the second position, causing the first internal extendable tang to bend;
a core;
the core including removal threads;
the removal threads interfacing with a driver;
whereby a user can use the driver to interface with the removal threads, pulling the tang system back into the externally-threaded body to permit removal of the externally-threaded body from the bone; and
whereby during extension of the first internal extendable tang and second internal extendable tang, the first internal extendable tang and the second internal extendable tang separate, extending in different directions separated by an acute angle.

6. The device with an externally-threaded body of claim 5, wherein:
the second position of the first internal extendable tang is not parallel to the externally-threaded body, but instead extended at an angle with respect to the externally-threaded body;
whereby the first internal extendable tang prevents rotation of the externally-threaded body.

7. The device with an externally-threaded body of claim 5, further comprising:
the one or more tang exit guide surfaces interfacing with the first internal extendable tang as it extends beyond the externally-threaded body and the second internal extendable tang as it extends beyond the externally-threaded body, causing the first internal extendable tang and the second internal extendable tang to change from a straight shape to a curved shape.

8. A bone screw with a first post-insertion locking tang, the bone screw comprising:
a body with an internal channel;
a tang system sliding within the internal channel;
the tang system including the first post-insertion locking tang;
the first post-insertion locking tang hidden during placement of the bone screw in a first position, and extendable after placement of the bone screw in a second position;
the tang system includes a second post-insertion locking tang;
the second post-insertion locking tang adjacent to the first post-insertion locking tang when the first post-insertion locking tang is in the first position;
the second post-insertion locking tang separated from the first post-insertion locking tang by an acute angle when the first post-insertion locking tang is the second position;
a tang exit portal;
the first post-insertion locking tang passing through the tang exit portal when moving between the first position within the body, and the second position extending beyond the body;
one or more tang exit guide surfaces;
the one or more tang exit guide surfaces changing a shape of the first post-insertion locking tang as it moves to the second position, causing the first post-insertion locking tang to bend;
a core;
the core including removal threads;
the removal threads interfacing with a driver;
whereby a user can use the driver to interface with the removal threads, pulling the tang system back into the body to permit removal of the body from a bone; and
whereby during extension of the first post-insertion locking tang and second post-insertion locking tang, the first post-insertion locking tang and the second post-insertion locking tang separate, extending in different directions separated by the acute angle, thus increasing fixation of the bone screw with respect to a bone.

9. The bone screw of claim 8, wherein:
the second position of the first post-insertion locking tang is not parallel to the body, but instead extended at an angle with respect to the body;
whereby the first post-insertion locking tang prevents rotation of the body.

10. The bone screw of claim 8, further comprising:
the one or more tang exit guide surfaces interfacing with the first post-insertion locking tang as it extends beyond the body and the second post-insertion locking tang as it extends beyond the body, causing the first post-insertion locking tang and the second post-insertion locking tang to change from a straight shape to a curved shape.

* * * * *